(12) United States Patent
Sun

(10) Patent No.: US 10,751,321 B2
(45) Date of Patent: Aug. 25, 2020

(54) PHARMACEUTICAL COMPOSITION CONTAINING GINKGOLIDE B AND ADP RECEPTOR ANTAGONIST, PREPARATION METHOD THEREOF AND USE THEREOF

(71) Applicant: CHENGDU BAIYU PHARMACEUTICAL CO., LTD, Chengdu, Sichuan (CN)

(72) Inventor: Yi Sun, Chengdu (CN)

(73) Assignee: CHENGDU BAIYU PHARMACEUTICAL CO., LTD, Sichuan (CN)

( * ) Notice: Subject to any disclaimer, the term of this patent is extended or adjusted under 35 U.S.C. 154(b) by 0 days.

(21) Appl. No.: 16/244,593

(22) Filed: Jan. 10, 2019

(65) Prior Publication Data

US 2019/0142794 A1    May 16, 2019

Related U.S. Application Data

(63) Continuation of application No. 15/522,681, filed as application No. PCT/CN2015/093083 on Oct. 28, 2015, now Pat. No. 10,322,105.

(30) Foreign Application Priority Data

Oct. 30, 2014  (CN) .......................... 2014 1 0606767

(51) Int. Cl.
*A61K 31/365* (2006.01)
*A61K 31/4365* (2006.01)
*A61K 45/06* (2006.01)
*A61K 31/519* (2006.01)

(52) U.S. Cl.
CPC ........ *A61K 31/365* (2013.01); *A61K 31/4365* (2013.01); *A61K 31/519* (2013.01); *A61K 45/06* (2013.01)

(58) Field of Classification Search
CPC .................................................. A61K 31/365
See application file for complete search history.

(56) References Cited

U.S. PATENT DOCUMENTS 6,383,528 B1    5/2002   Ann et al.

FOREIGN PATENT DOCUMENTS

| CN | 1283119 A | 2/2001 |
|----|-----------|--------|
| CN | 1768753 A | 5/2006 |

OTHER PUBLICATIONS

Shi, Xubo et al., Clinical Forcus, Mar. 4, 2009, pp. 461-464.*
Wu, Yaning et al. Chinese Journal of Clinical Pharmacology and Therapeutics (2010) pp. 1434-1440.*
Shi Xubo et al. "Application Status and Prospect of Adenosine Diphosphate Receptor Antagonist", Clinical Focus, vol. 24, No. 6., pp. 461-464, Mar. 20, 2009.
Wu, Yaning et al. "Progression of ADP Receptor Inhibitors Antiplatelet Drugs." Chinese Journal of Clinical Pharmacology and Therapuetics, vol. 15, No. 12, pp. 1434-1440, Dec. 31, 2010.
Feb. 2, 2016 Search Report issued in International Patent Application No. PCT/CN2015/093083.
Feb. 2, 2016 Written Opinion issued in International Patent Application No. PCT/CN2015/093083.
Nov. 16, 2017 Office Action issued in Chinese Application No. 201510714325.0.
Jul. 16, 2018 Office Action issued in Chinese Application No. 201510714325.0.

* cited by examiner

*Primary Examiner* — Paul V Ward
(74) *Attorney, Agent, or Firm* — Oliff PLC

(57) ABSTRACT

A pharmaceutical composition containing ginkgolide B and an ADP receptor antagonist, a preparation method thereof and use thereof in preparation of antiplatelet drugs, wherein the ADP receptor antagonist is clopidogrel, prasugrel, ticagrelor and/or ticlopidine.

12 Claims, No Drawings

PHARMACEUTICAL COMPOSITION CONTAINING GINKGOLIDE B AND ADP RECEPTOR ANTAGONIST, PREPARATION METHOD THEREOF AND USE THEREOF

CROSS-REFERENCE TO RELATED APPLICATIONS

This is a Continuation of application Ser. No. 15/522,681 filed Apr. 27, 2017, which in turn is allowed and is a national stage entry of PCT/CN2015/093083 filed Oct. 28, 2015, which claims priority to CN 201410606767.9 filed Oct. 30, 2014. The disclosure of each of the prior applications is hereby incorporated by reference herein in its entirety.

TECHNICAL FIELD

The invention relates to a pharmaceutical composition containing Ginkgolide B.

BACKGROUND OF THE INVENTION

Clopidogrel, Prasugrel, Ticagrelor and Ticlopidine are adenosine diphosphate (ADP) receptor antagonists, which can inhibit ADP-mediated platelet activation and aggregation.

Clopidogrel, (S)-alpha-(2-chlorphenyl)-6,7-dihydrothieno [3,2 -c]pyridine-5-(4H)acetate hydrogen sulfate, molecular formula $C_{16}H_{16}ClNO_2SH_2SO_4$, molecular weight 419.9. Common side effects include rash (4%), diarrhea (5%), abdominal pain (6%), dyspepsia (5%), intracranial hemorrhage (0.4%), digestive tract hemorrhage (2%), serious granulocyte reduction (0.04%). Results are mainly from a large clinical trial (CAPRIE). The general tolerance of clopidogrel in the study is equivalent to that of ASA, and is unrelated to age, race and gender. Hemorrhagic diseases include gastrointestinal hemorrhage, purpura, congestion, hematoma, epistaxis, hematuria, ocular hemorrhage (mainly conjunctival hemorrhage) and intracranial hemorrhage. The severe bleeding rate of Clopidogrel-treated patients is 1.4%. In blood system, it includes severe neutrophile granulocyte reduction, aplastic anemia and serious platelet reduction, which are relatively rare.

Prasugrel, 2-[2-(acetoxyl)-6,7-dihydrothieno[3,2-c]pyridine-5(4H)-yl]-1-cyclopropyl-2-(2-fluorophenyl))ethanone, molecular formula: $C_{20}H_{20}FNO_3S$, molecular weight: 373.44. Clinically, it is used to treat cardiovascular and cerebrovascular diseases such as heart failure, stroke, unstable angina. To patients with acute coronary syndrome and requiring percutaneous coronary intervention surgery, the effect of Prasugrel is better than that of Clopidogrel, but the carcinogenesis risk is high, and the hemorrhage risk of prasurel is also higher than that of Clopidogrel.

Ticagrelor, molecular formula: $C_{23}H_{28}F_2N_6O_4S$, molecular weight: 522.57, (1S,2S,3R,5S)-3-[7-[(1R,2S)-2-(3,4-Difluorophenyl)cycloprolamino]-5-(propyl sulfanyl)-3H-[1,2,3]triazolo[4,5-d]pyrimidin-3-yl]-5-(2-hydroxyethoxy) cyclopenane-1,2-diol. In patients treated with Ticagrelor, the most frequently reported side effects are dyspnea, contusion and nasal hemorrhage, and the occurrence rate of Ticagrelor is higher than that of the Clopidogrel. Other common side effects include gastrointestinal hemorrhage, subcutaneous or dermis bleeding, blood stasis and operation site bleeding. Occasional side effects include intracranial hemorrhage, dizziness and headache, eye hemorrhage, hemoptysis, hematemesis, gastrointestinal ulcer hemorrhage, hemorrhoids bleeding, gastritis, oral bleeding, emesis, diarrhea, abdominal pain, nausea, dyspepsia, itching, rash, urethra and vagina bleeding, and postoperative bleeding. Rare side effects include: hyperuricemia, consciousness disorder, sensory abnormality, ear hemorrhage, dizziness and dizziness, post-peritoneal bleeding, constipation, hemarthrosis, blood creatinine rise, wound bleeding, traumatic bleeding, wound bleeding, wound bleeding, blood creatinine rise, wound bleeding, traumatic bleeding. In the PLATO study, the occurrence rate of interventricular interval among Ticagrelor-treated patients in the acute stage is 60%; the occurrence rate of the interventricular interval after one month is 2.2%.

Ticlopidine, molecular formula: $C_{14}H_{14}ClNS$; molecular weight: 263.79. It is mainly used for chronic thromboangiitis obliterans, obliterative arteriosclerosis, myocardial infarction, cerebral ischemia and so on. It has an inhibitory effect on platelet aggregation induced by collagen, thrombin, arachidonic acid, epinephrine, and platelet activation factor and the like. Moreover, it has a certain depolymerization effect. Common side effects include digestive tract symptoms (such as nausea, abdominal discomfort and diarrhea) and rash. The occurrence rate is about 10% and can be reduced by a postprandial administration. Common side effects also include hemorrhage and gastrointestinal disease such as nausea, emesis and diarrhea, which can be alleviated by a postprandial administration. Allergic reactions, such as urticaria and rash, mainly occur in the first month of treatment. Hematological changes such as leukopenia, granulocyte deficiency, whole blood cell reduction, erythroleukemia. If any early sign is found, the medicine should be immediately stopped. Cholestasis jaundice and the like can also be found occasionally.

Therefore, how to reduce the side effect through reducing the use of Clopidogrel, Prasugrel, Ticagrelor and Ticlopidine without losing the treatment effect requires a solution.

Ginkgolide B is the most potent antagonist against platelet activation factor that has been found heretofore. It has been used to treat phlegm and blood stasis obstruction of ischemic stroke. However, its price is high and clinical usage cost is high.

SUMMARY OF THE INVENTION

The invention aims to provide a novel pharmaceutical composition with a synergistic effect for overcoming adverse effect of adenosine diphosphate receptor antagonist such as Clopidogrel, Prasugrel, Ticagrelor or Ticlopidine which is used for anti-platelet aggregation respectively.

The present invention provides a pharmaceutical composition containing Ginkgolide B, wherein the pharmaceutical composition comprises Ginkgolide B and platelet aggregation inhibitor.

The platelet aggregation inhibitor is adenosine diphosphate receptor antagonist.

The adenosine diphosphate receptor antagonist is Clopidogrel, Prasugrel, Ticagrelor and/or Ticlopidine.

Ginkgolide B is in an amount of 1-20 parts by weight, and any one of Clopidogrel, Prasugrel, Ticagrelor and Ticlopidine is in an amount of 50-500 parts by weight; preferably, Ginkgolide B is in an amount of 5-15 parts by weight and any one of Clopidogrel, Prasugrel, Ticagrelor and Ticlopidine is in an amount of 100-400 parts by weight; more preferably, Ginkgolide B is in an amount of 8-12 parts by weight and any one of Clopidogrel, Prasugrel, Ticagrelor and Ticlopidine is in an amount of 150-300 parts by weight; even more preferably, Ginkgolide B is in an amount of 10 parts by weight and any one of Clopidogrel, Prasugrel, Ticagrelor and Ticlopidine is in an amount of 200 parts by weight.

The present invention also provides a method for preparing the pharmaceutical composition, comprising the following steps:

S1: weighing out raw materials of Ginkgolide B and platelet aggregation inhibitor according to the predetermined parts by weight;

S2: mixing the raw materials, and adding a pharmaceutically acceptable auxiliary to prepare a common pharmaceutical preparation.

Wherein the pharmaceutical acceptable auxiliary is selected from the group consisting of: starch, pregelatinized starch, lactose, sucrose, talcum powder, dextrin, cyclodextrin, microcrystalline cellulose, croscarmellose sodium, sodium carboxymethyl starch, low substituted hydroxypropyl cellulose, cross-linked povidone, glucose, meglumine, magnesium stearate, dextran, glycerol, ethanol, propylene glycol, polyethylene glycol, mannitol, sorbitol, xylitol, fiber vegetable oil, sodium benzoate, sodium salicylate, hydrochloric acid, citric acid, sodium citrate, sodium dihydrogen phosphate, disodium hydrogen phosphate, gelatin, lecithin and vitamin C.

Wherein the pharmaceutical formulation comprises: tablet, capsule, soft capsule, oral liquid, granules, pills, dripping pills, powder, paste, pellets, injections, suppository, patch, drop, spray, cream, suspension, tincture, emulsion, solution injection, powder injection, targeting formulation, sustained-release formulation and controlled-release formulation.

The present invention also provides use of the pharmaceutical combination in the manufacturing of a medicament for anti-platelet aggregation.

The present invention also provides use of the pharmaceutical combination of Ginkgolide B and platelet aggregation inhibitor in the manufacturing of a medicament for anti-platelet aggregation.

The platelet aggregation inhibitor is adenosine diphosphate receptor antagonist. The adenosine diphosphate receptor antagonist is Clopidogrel, Prasugrel, Ticagrelor and/or Ticlopidine.

Ginkgolide B is in an amount of 1-20 parts by weight, and any one of Clopidogrel, Prasugrel, Ticagrelor and Ticlopidine is in an amount of 50-500 parts by weight; preferably, Ginkgolide B is in an amount of 5-15 parts by weight and any one of Clopidogrel, Prasugrel, Ticagrelor and Ticlopidine is in an amount of 100-400 parts by weight; more preferably, Ginkgolide B is in an amount of 8-12 parts by weight and any one of Clopidogrel, Prasugrel, Ticagrelor and Ticlopidine is in an amount of 150-300 parts by weight; even more preferably, Ginkgolide B is in an amount of 10 parts by weight and any one of Clopidogrel, Prasugrel, Ticagrelor and Ticlopidine is in an amount of 200 parts by weight.

The pharmaceutical composition of the present invention comprising Ginkgolide B and adenosine diphosphate receptor antagonist as active ingredients, functions through inhibiting ADP inducing platelet activation and aggregation. Ginkgolide B can remarkably promote the anti-platelet aggregation function of adenosine diphosphate receptor antagonist. Using Ginkgolide B and adenosine diphosphate receptor antagonist resulting a synergistic effect, less dosage of adenosine diphosphate receptor antagonist, better potency, reducing cost and side effect and providing a better choice for clinical study.

The pharmaceutical composition of the present invention is characterized in a novel formula, simple components, a clear action mechanism, a remarkable effect, and hard to produce tolerance, and a large-scale industrial production can be realized.

Ginkgolide B and adenosine diphosphate receptor antagonist are combined in the present invention, and a synergistic effect and an effective platelet aggregation inhibition are achieved. When used in clinic, less dosage of adenosine diphosphate receptor antagonist is needed and resulting a milder side effect originating from large dosage. The dosage of Ginkgolide B is also reduced, as well as the cost. The use of the pharmaceutical combination in clinic is quite promising.

Apparently, according to the above-mentioned disclosure of the present invention, other various modifications, substitutions or alterations can be made without departing from the basic technical concept of the present invention on the basis of the ordinary technical knowledge and common means of the art.

The above disclosure of the present invention is further described in detail in the following embodiments. The following embodiments are for better understanding of the present invention, not to limit the invention to the preferred embodiments. Any technique derived from the present invention, falls within the protection scope of the present invention.

DETAILED DESCRIPTION OF EMBODIMENTS

The Ginkgolide B monomer of the present invention can be obtained by purchasing a commercially available product, or obtained by separating and purifying the Ginkgolide using an existing method; Clopidogrel, Prasugrel, Ticagrelor and Ticlopidine can also be obtained by purchasing a commercially available product or synthesized using an existing method. All monomeric compounds are consistent with the structure of corresponding reference substance, and the purity of all the monomer compounds is over 95% analyzed by HPLC.

Clopidogrel, Prasugrel, Ticagrelor and Ticlopidine

Embodiment 1

10 parts by weight of Ginkgolide B 200 parts by weight of Clopidogrel

Pharmaceutically acceptable auxiliary

Mixing the raw materials, then adding the pharmaceutically acceptable auxiliary to the raw materials to prepare pills according to a conventional process.

Embodiment 2

15 parts by weight of Ginkgolide B 400 parts by weight of Clopidogrel

Pharmaceutically acceptable auxiliary

Mixing the raw materials, then adding the pharmaceutically acceptable auxiliary to the raw materials to prepare capsule or soft capsule according to a conventional process.

Embodiment 3

1 parts by weight of Ginkgolide B
50 parts by weight of Clopidogrel
Pharmaceutically acceptable auxiliary Mixing the raw materials, then adding the pharmaceutically acceptable auxiliary to the raw materials to prepare tablet according to a conventional process.

Embodiment 4

8 parts by weight of Ginkgolide B
150 parts by weight of Clopidogrel
Pharmaceutically acceptable auxiliary Mixing the raw materials, then adding the pharmaceutically acceptable auxiliary to the raw materials to prepare oral liquid according to a conventional process.

Embodiment 5

12 parts by weight of Ginkgolide B
300 parts by weight of Clopidogrel
Pharmaceutically acceptable auxiliary Mixing the raw materials, then adding the pharmaceutically acceptable auxiliary to the raw materials to prepare dripping pills according to a conventional process.

Embodiment 6

12 parts by weight of Ginkgolide B
150 parts by weight of Clopidogrel
Pharmaceutically acceptable auxiliary Mixing the raw materials, then adding the pharmaceutically acceptable auxiliary to the raw materials to prepare spray according to a conventional process.

Embodiment 7

1 parts by weight of Ginkgolide B
500 parts by weight of Clopidogrel
Pharmaceutically acceptable auxiliary Mixing the raw materials, then adding the pharmaceutically acceptable auxiliary to the raw materials to prepare solution injection or powder injection according to a conventional process.

Embodiment 8

10 parts by weight of Ginkgolide B
200 parts by weight of Clopidogrel
Pharmaceutically acceptable auxiliary Mixing the raw materials, then adding the pharmaceutically acceptable auxiliary to the raw materials to prepare sustained-release formulation and controlled-release formulation according to a conventional process.

Embodiment 9

10 parts by weight of Ginkgolide B
200 parts by weight of Clopidogrel
Pharmaceutically acceptable auxiliary Mixing the raw materials, then adding the pharmaceutically acceptable auxiliary to the raw materials to prepare targeting formulation according to a conventional process.

Embodiment 10

10 parts by weight of Ginkgolide B
200 parts by weight of Clopidogrel
Pharmaceutically acceptable auxiliary Mixing the raw materials, then adding the pharmaceutically acceptable auxiliary to the raw materials to prepare granules or suspension according to a conventional process.

Embodiment 11

10 parts by weight of Ginkgolide B
200 parts by weight of Prasugrel
Pharmaceutically acceptable auxiliary Mixing the raw materials, then adding the pharmaceutically acceptable auxiliary to the raw materials to prepare pills according to a conventional process.

Embodiment 12

15 parts by weight of Ginkgolide B
400 parts by weight of Prasugrel
Pharmaceutically acceptable auxiliary Mixing the raw materials, then adding the pharmaceutically acceptable auxiliary to the raw materials to prepare capsule or soft capsule according to a conventional process.

Embodiment 13

20 parts by weight of Ginkgolide B
500 parts by weight of Prasugrel
Pharmaceutically acceptable auxiliary Mixing the raw materials, then adding the pharmaceutically acceptable auxiliary to the raw materials to prepare tablet according to a conventional process.

Embodiment 14

15 parts by weight of Ginkgolide B
400 parts by weight of Prasugrel
Pharmaceutically acceptable auxiliary Mixing the raw materials, then adding the pharmaceutically acceptable auxiliary to the raw materials to prepare oral liquid according to a conventional process.

Embodiment 15

12 parts by weight of Ginkgolide B
300 parts by weight of Prasugrel
Pharmaceutically acceptable auxiliary Mixing the raw materials, then adding the pharmaceutically acceptable auxiliary to the raw materials to prepare dripping pills according to a conventional process.

Embodiment 16

12 parts by weight of Ginkgolide B
150 parts by weight of Prasugrel
Pharmaceutically acceptable auxiliary Mixing the raw materials, then adding the pharmaceutically acceptable auxiliary to the raw materials to prepare spray according to a conventional process.

Embodiment 17

1 parts by weight of Ginkgolide B
500 parts by weight of Prasugrel
Pharmaceutically acceptable auxiliary Mixing the raw materials, then adding the pharmaceutically acceptable auxiliary to the raw materials to prepare solution injection or powder injection according to a conventional process.

Embodiment 18

10 parts by weight of Ginkgolide B
200 parts by weight of Prasugrel
Pharmaceutically acceptable auxiliary Mixing the raw materials, then adding the pharmaceutically acceptable auxiliary to the raw materials to prepare sustained-release formulation and controlled-release formulation according to a conventional process.

Embodiment 19

10 parts by weight of Ginkgolide B
200 parts by weight of Prasugrel
Pharmaceutically acceptable auxiliary Mixing the raw materials, then adding the pharmaceutically acceptable auxiliary to the raw materials to prepare targeting formulation according to a conventional process.

Embodiment 20

10 parts by weight of Ginkgolide B
200 parts by weight of Prasugrel
Pharmaceutically acceptable auxiliary Mixing the raw materials, then adding the pharmaceutically acceptable auxiliary to the raw materials to prepare granules or suspension according to a conventional process.

Embodiment 21

10 parts by weight of Ginkgolide B
200 parts by weight of Ticagrelor
Pharmaceutically acceptable auxiliary Mixing the raw materials, then adding the pharmaceutically acceptable auxiliary to the raw materials to prepare pills according to a conventional process.

Embodiment 22

15 parts by weight of Ginkgolide B
400 parts by weight of Ticagrelor
Pharmaceutically acceptable auxiliary Mixing the raw materials, then adding the pharmaceutically acceptable auxiliary to the raw materials to prepare capsule or soft capsule according to a conventional process.

Embodiment 23

20 parts by weight of Ginkgolide B
500 parts by weight of Ticagrelor
Pharmaceutically acceptable auxiliary Mixing the raw materials, then adding the pharmaceutically acceptable auxiliary to the raw materials to prepare tablet according to a conventional process.

Embodiment 24

15 parts by weight of Ginkgolide B
100 parts by weight of Ticagrelor
Pharmaceutically acceptable auxiliary Mixing the raw materials, then adding the pharmaceutically acceptable auxiliary to the raw materials to prepare oral liquid according to a conventional process.

Embodiment 25

10 parts by weight of Ginkgolide B
300 parts by weight of Ticagrelor
Pharmaceutically acceptable auxiliary Mixing the raw materials, then adding the pharmaceutically acceptable auxiliary to the raw materials to prepare dripping pills according to a conventional process.

Embodiment 26

12 parts by weight of Ginkgolide B
150 parts by weight of Ticagrelor
Pharmaceutically acceptable auxiliary Mixing the raw materials, then adding the pharmaceutically acceptable auxiliary to the raw materials to prepare spray according to a conventional process.

Embodiment 27

1 parts by weight of Ginkgolide B
500 parts by weight of Ticagrelor
Pharmaceutically acceptable auxiliary Mixing the raw materials, then adding the pharmaceutically acceptable auxiliary to the raw materials to prepare solution injection or powder injection according to a conventional process.

Embodiment 28

10 parts by weight of Ginkgolide B
200 parts by weight of Ticagrelor
Pharmaceutically acceptable auxiliary Mixing the raw materials, then adding the pharmaceutically acceptable auxiliary to the raw materials to prepare sustained-release formulation and controlled-release formulation according to a conventional process.

Embodiment 29

10 parts by weight of Ginkgolide B
200 parts by weight of Ticagrelor
Pharmaceutically acceptable auxiliary Mixing the raw materials, then adding the pharmaceutically acceptable auxiliary to the raw materials to prepare targeting formulation according to a conventional process.

Embodiment 30

10 parts by weight of Ginkgolide B
200 parts by weight of Ticagrelor
Pharmaceutically acceptable auxiliary Mixing the raw materials, then adding the pharmaceutically acceptable auxiliary to the raw materials to prepare granules or suspension according to a conventional process.

Embodiment 31

12 parts by weight of Ginkgolide B
300 parts by weight of Ticlopidine
Pharmaceutically acceptable auxiliary Mixing the raw materials, then adding the pharmaceutically acceptable auxiliary to the raw materials to prepare spray according to a conventional process.

Embodiment 32

20 parts by weight of Ginkgolide B
500 parts by weight of Ticlopidine
Pharmaceutically acceptable auxiliary Mixing the raw materials, then adding the pharmaceutically acceptable auxiliary to the raw materials to prepare solution injection or powder injection according to a conventional process.

Embodiment 33

10 parts by weight of Ginkgolide B
200 parts by weight of Ticlopidine
Pharmaceutically acceptable auxiliary Mixing the raw materials, then adding the pharmaceutically acceptable auxiliary to the raw materials to prepare sustained-release formulation and controlled-release formulation according to a conventional process.

Embodiment 34

1 parts by weight of Ginkgolide B
50 parts by weight of Ticlopidine
Pharmaceutically acceptable auxiliary Mixing the raw materials, then adding the pharmaceutically acceptable auxiliary to the raw materials to prepare targeting formulation according to a conventional process.

Embodiment 35

15 parts by weight of Ginkgolide B
400 parts by weight of Ticlopidine
Pharmaceutically acceptable auxiliary Mixing the raw materials, then adding the pharmaceutically acceptable auxiliary to the raw materials to prepare granules or suspension according to a conventional process.

Embodiment 36

8 parts by weight of Ginkgolide B
150 parts by weight of Ticlopidine
Pharmaceutically acceptable auxiliary Mixing the raw materials, then adding the pharmaceutically acceptable auxiliary to the raw materials to prepare spray according to a conventional process.

The beneficial effects of the present invention are further described by following experimental examples.

EXPERIMENTAL EXAMPLE 1

Study of Composition of Ginkgolide B and ADP Receptor Antagonist in Inhibition of Rabbit Platelet Aggregation Effect 1 Materials and Methods
1.1. Experimental Animals:
448 Japanese large-ear white rabbits with a weight of (2.0±0.2) kg, half male and half female, were provided by Chongqing Medical University Experimental Animal Center [animal certification number: XCXK (Yu) 20020001].

1.2. Experimental Medicine:
Ginkgolide B (self-made), Clopidogrel (self-made), Prasugrel (self-made), Ticagrelor (self-made) and Ticlopidine (self-made), Jinnaduo injection (Ginkgolide extraction injection), Extraction combination (Jinnaduo:Ticlopidine=10:200), Composition 1 (Ginkgolide B:Clopidogrel=10:200), Composition 2 (Ginkgolide B:Clopidogrel=1:50), Composition 3 (Ginkgolide B:Clopidogrel=1:500), Composition 4 (Ginkgolide B:Clopidogrel=20:50), Composition 5 (Ginkgolide B:Clopidogrel=20:500), Composition 6 (Ginkgolide B:Clopidogrel=5:400), Composition 7 (Ginkgolide B:Clopidogrel=15:100), Composition 8 (Ginkgolide B:Clopidogrel=15:400), Composition 9 (Ginkgolide B:Clopidogrel=8:150), Composition 10 (Ginkgolide B: Clopidogrel=8:300), Composition 11 (Ginkgolide B:Clopidogrel=12:150), Composition 12 (Ginkgolide B:Clopidogrel=12:300), Composition 13 (Ginkgolide B:Prasugrel=10:200), Composition 14 (Ginkgolide B:Prasugrel=1:50), Composition 15 (Ginkgolide B:Prasugrel=1:500), Composition 16 (Ginkgolide B:Prasugrel=20:50), Composition 17 (Ginkgolide B:Prasugrel=20:500), Composition 18 (Ginkgolide B:Prasugrel=5:400), Composition 19 (Ginkgolide B:Prasugrel=15:100), Composition 20 (Ginkgolide B:Prasugrel=15:400), Composition 21 (Ginkgolide B:Prasugrel=8:150), Composition 22 (Ginkgolide B:Prasugrel=8:300), Composition 23 (Ginkgolide B:Prasugrel=12:150), Composition 24 (Ginkgolide B:Prasugrel=12:300), Composition 25 (Ginkgolide B:Ticagrelor=10:200), Composition 26 (Ginkgolide B:Ticagrelor=1:50), Composition 27 (Ginkgolide B:Ticagrelor=1:500), Composition 28 (Ginkgolide B:Ticagrelor=20:50), Composition 29 (Ginkgolide B:Ticagrelor=20:500), Composition 30 (Ginkgolide B:Ticagrelor=5:400), Composition 31 (Ginkgolide B:Ticagrelor=15:100), Composition 32 (Ginkgolide B:Ticagrelor=15:400), Composition 33 (Ginkgolide B:Ticagrelor=8:150), Composition 34 (Ginkgolide B:Ticagrelor=8:300), Composition 35 (Ginkgolide B:Ticagrelor=12:150), Composition 36 (Ginkgolide B:Ticagrelor=12:300), Composition 37 (Ginkgolide B:Ticlopidine=10:200), Composition 38 (Ginkgolide B:Ticlopidine=1:50), Composition 39 (Ginkgolide B:Ticlopidine=1:500), Composition 40 (Ginkgolide B:Ticlopidine=20:50), Composition 41 (Ginkgolide B:Ticlopidine=20:500), Composition 42 (Ginkgolide B:Ticlopidine=5:400), Composition 43 (Ginkgolide B:Ticlopidine=15:100), Composition 44 (Ginkgolide B:Ticlopidine=15:400), Composition 45 (Ginkgolide B:Ticlopidine=8:150), Composition 46 (Ginkgolide B:Ticlopidine=8:300), Composition 47 (Ginkgolide B:Ticlopidine=12:150), Composition 48 (Ginkgolide B:Ticlopidine=12:300).

1.3 Reagents and Instruments
Platelet activation factors (PAF) (cayman, lot number: 011219) was dissolved in the Tris-NaCl solution containing 0.25% of calf serum albumin at a pH of 7.6, to a final concentration of 3.6 nmoL/L; sodium citrate (Beijing Zhongshanjinqiao Biotechnology Company, lot number: 20130117) dissolved in the distilled water with 3.8% concentration; rabbit β-thromboglobulin (β-TG) ELISA kit (FOCUS, lot number: 20130224), rabbit platelet factor 4 (PF-4) ELISA kit (FOCUS, lot number: 20130301). TYXN-96 multifunctional intelligent aggregometer (Shanghai General Technique Research Institute); Scanning electron microscope S-3000 N (Hitachi Limited); ELX-800 Absorbance Reader (BioTek Instruments, Inc.).

1.4 Groups and Administration Method
448 Japanese large-ear white rabbits were randomly assigned to 56 groups, with 8 rabbits in each group: (1) Saline group, (2) Ginkgolide B group, (3) Clopidogrel group, (4) Prasugrel group, (5) Ticagrelor group, (6) Ticlopidine group, (7) Jinnaduo injection (Ginkgolide extraction injection) group, (8) Extraction combination group (Jinnaduo:Ticlopidine=10:200), (9) Composition group, (10) Composition 2 group, (11) Composition 3 group, (12) Composition 4 group, (13) Composition 5 group, (14) Composition 6 group, (15) Composition 7 group, (16) Composition 8 group, (17) Composition 9 group, (18) Composition 10 group, (19) Composition 11 group, (20) Composition 12 group, (21) Composition 13 group, (22) Composition 14 group, (23) Composition 15 group, (24) Composition 16 group, (25) Composition 17 group, (26) Composition 18 group, (27) Composition 19 group, (28) Composition 20 group, (29) Composition 21 group, (30) Composition 22 group, (31) Composition 23 group, (32) Composition 24 group, (33) Composition 25 group, (34) Composition 26 group, (35) Composition 27 group, (36) Composition 28 group, (37) Composition 29 group, (38) Composition 30 group, (39) Composition 31 group, (40) Composition 32 group, (41) Composition 33 group, (42) Composition 34 group, (43) Composition 35 group, (44) Composition 36 group, (45) Composition 37 group, (46) Composition 38 group, (47) Composition 39 group, (48) Composition 40 group, (49) Composition 41 group, (50) Composition 42 group, (51) Composition 43 group, (52) Composition 44 group, (53) Composition 45 group, (54) Composition 46 group, (55) Composition 47 group, (56) Composition 48 group. All groups were administered with a clinically used route and dosage for 7 days continuously. The dosage is showed in the following Table:

| Group | Dosage | Daily dosing frequency |
| --- | --- | --- |
| Saline | 2 ml | 1 |
| Ginkgolide B | 5.0 mg/kg | 1 |
| Clopidogrel | 5.0 mg/kg | 1 |
| Prasugrel | 5.0 mg/kg | 1 |
| Ticagrelor | 5.0 mg/kg | 1 |
| Ticlopidine | 5.0 mg/kg | 1 |
| Jinnaduo | 5.0 mg/kg | 1 |
| Extraction combination | 5.0 mg/kg | 1 |
| Composition 1 | 5.0 mg/kg | 1 |
| Composition 2 | 5.0 mg/kg | 1 |
| Composition 3 | 5.0 mg/kg | 1 |
| Composition 4 | 5.0 mg/kg | 1 |
| Composition 5 | 5.0 mg/kg | 1 |
| Composition 6 | 5.0 mg/kg | 1 |
| Composition 7 | 5.0 mg/kg | 1 |
| Composition 8 | 5.0 mg/kg | 1 |
| Composition 9 | 5.0 mg/kg | 1 |
| Composition 10 | 5.0 mg/kg | 1 |
| Composition 11 | 5.0 mg/kg | 1 |
| Composition 12 | 5.0 mg/kg | 1 |
| Composition 13 | 5.0 mg/kg | 1 |
| Composition 14 | 5.0 mg/kg | 1 |
| Composition 15 | 5.0 mg/kg | 1 |
| Composition 16 | 5.0 mg/kg | 1 |
| Composition 17 | 5.0 mg/kg | 1 |
| Composition 18 | 5.0 mg/kg | 1 |
| Composition 19 | 5.0 mg/kg | 1 |
| Composition 20 | 5.0 mg/kg | 1 |
| Composition 21 | 5.0 mg/kg | 1 |
| Composition 22 | 5.0 mg/kg | 1 |
| Composition 23 | 5.0 mg/kg | 1 |
| Composition 24 | 5.0 mg/kg | 1 |
| Composition 25 | 5.0 mg/kg | 1 |
| Composition 26 | 5.0 mg/kg | 1 |
| Composition 27 | 5.0 mg/kg | 1 |
| Composition 28 | 5.0 mg/kg | 1 |
| Composition 29 | 5.0 mg/kg | 1 |
| Composition 30 | 5.0 mg/kg | 1 |
| Composition 31 | 5.0 mg/kg | 1 |
| Composition 32 | 5.0 mg/kg | 1 |
| Composition 33 | 5.0 mg/kg | 1 |
| Composition 34 | 5.0 mg/kg | 1 |
| Composition 35 | 5.0 mg/kg | 1 |
| Composition 36 | 5.0 mg/kg | 1 |
| Composition 37 | 5.0 mg/kg | 1 |
| Composition 38 | 5.0 mg/kg | 1 |
| Composition 39 | 5.0 mg/kg | 1 |
| Composition 40 | 5.0 mg/kg | 1 |
| Composition 41 | 5.0 mg/kg | 1 |
| Composition 42 | 5.0 mg/kg | 1 |
| Composition 43 | 5.0 mg/kg | 1 |
| Composition 44 | 5.0 mg/kg | 1 |
| Composition 45 | 5.0 mg/kg | 1 |
| Composition 46 | 5.0 mg/kg | 1 |
| Composition 47 | 5.0 mg/kg | 1 |
| Composition 48 | 5.0 mg/kg | 1 |

1. 5. Study of Platelet Aggregation Rate

After 7 days of administration, 10.5 ml of blood was taken from the heart of each animal, wherein 1.5 ml of plasma was used for taking serum and the rest 9 ml of plasma was subjected to 3.8% sodium citrate at 1:9 for anticoagulation, centrifuging for 10 minutes at 800 r/min, and taking the supernatant to obtain platelet-rich plasma (PRP), wherein 100 µl of the PRP was taken for electron microscope examination, and the rest of the PRP was used for detecting of the platelet aggregation rate; the remaining portion was centrifuged for 15 min at a speed of 3000 r/min, and platelet-depleted plasma (PPP) was obtained. PPP was used to adjust the number of platelet in PRP, to be at $360 \times 10^9$/L. The platelet aggregation rate was recorded at 1 min, 5 min of addition of 10 µL of PAF inducer and the maximum platelet aggregation rate was recorded after the addition of PAR 1. 6. Scanning Electron Microscopy Study of Platelet The 100 µL of PRP was placed in a silicification EP tube, and 1 µL of PAF was added to induce aggregation of platelets for 15 minutes, the PRP was then placed on a copper mesh sample support laid with a Formar membrane, incubating at 37° C. for 10 min, washing with ultrapure water, fixing with 3% glutaraldehyde for 5 minutes, rewashing with ultrapure water. After the sample on the copper mesh was naturally dried, a layer of 20 nm gold film was plated on the surface of the sample, and the cell morphology was studied with an electron microscope S-3000N. 100 of platelets were observed and calculated the ratio of each type of platelet. The types of platelet under the electron microscope includes: (1) Circle type appears circular or oval, with small size, compact center, large core and low and narrow transparent periphery zone. (2) Tree like type has a single or a plurality of elongated or sheet-shaped sometimes branched foot protrudes from the dense center. (3) Flat type has a dense core in the center and a wide transparent peripheral zone which has a smooth periphery or small bulges. (4) Aggregated-type is usually composed of several to dozens of platelets, with different sizes of the aggregates, wherein the platelets are mutually connected, some of the platelets are integrally fused into a whole, and the foot processes of the peripheral part are prominent.

1.7 Determination of PF-4 and β-TG levels in serum

1 µL of PAF was added to 1.5 mL of plasma for induction of release of PF-4 and β-TG. The plasma was rested at 4° C. for 4 hours, and 200 µL of serum was taken for detection. The specific operation is carried out according to the kit specification, and the result was read by the Absorbance Reader.

1.8 Statistical Analysis

The experimental results were showed in the form of mean value±standard deviation ($\bar{x}\pm s$). The statistical analysis is carried out using SPSS 18.0 software, and the platelet aggregation rates, the percentage of types of platelet morphology and the concentration of PF-4 and β-TG were analyzed using two-sample t-test. P-values<0.05 were considered statistically significant.

2. Results 2.1 Result of Platelet Aggregation Rate

The result is shown in Table.1:

TABLE 1

The aggregation effect of platelet inducing by PAF ($\bar{x} \pm s$, n = 8)

| Group | Dosage | 1 min | 5 min | MAX | Platelet aggregation inhibition rate (%) |
|---|---|---|---|---|---|
| Saline | 2 ml | 36.85 ± 6.14 | 68.32 ± 9.17 | 70.22 ± 11.40 | 0.00 |
| Ginkgolide B | 5.0 mg/kg | 21.36 ± 4.15** | 33.54 ± 5.48** | 38.86 ± 4.74** | 44.66 |
| Clopidogrel | 5.0 mg/kg | 35.27 ± 6.08 | 53.73 ± 8.46* | 60.96 ± 9.50 | 13.19 |
| Prasugrel | 5.0 mg/kg | 37.14 ± 8.59 | 55.56 ± 7.53 | 63.12 ± 5.47 | 10.11 |
| Ticagrelor | 5.0 mg/kg | 34.21 ± 5.75 | 60.50 ± 9.24 | 67.74 ± 9.36 | 3.53 |
| Ticlopidine | 5.0 mg/kg | 31.62 ± 5.77* | 58.34 ± 4.98* | 57.46 ± 5.71* | 18.17 |
| Jinnaduo | 5.0 mgl/kg | 30.51 ± 5.30* | 48.48 ± 8.79** | 51.60 ± 8.44** | 26.52 |
| Extraction combination | 5.0 mgl/kg | 30.71 ± 7.18 | 40.69 ± 6.75* | 50.94 ± 7.21* | 27.47 |
| Composition 1 | 5.0 mgl/kg | 24.54 ± 6.24** | 34.57 ± 7.36** | 38.75 ± 6.48** | 44.82 |
| Composition 2 | 5.0 mg/kg | 32.15 ± 6.57* | 42.65 ± 8.17* | 52.19 ± 5.89* | 25.68 |
| Composition 3 | 5.0 mg/kg | 34.41 ± 6.46* | 45.67 ± 6.79* | 55.16 ± 6.58* | 21.45 |
| Composition 4 | 5.0 mg/kg | 21.17 ± 7.15** | 35.78 ± 7.53** | 40.26 ± 6.45** | 42.67 |
| Composition 5 | 5.0 mg/kg | 35.64 ± 5.71* | 43.48 ± 7.54* | 50.64 ± 5.84* | 27.88 |
| Composition 6 | 5.0 mg/kg | 35.12 ± 5.24* | 45.28 ± 5.48 | 55.23 ± 7.19* | 21.35 |
| Composition 7 | 5.0 mg/kg | 22.27 ± 6.59** | 35.61 ± 8.47** | 40.56 ± 6.87** | 42.24 |
| Composition 8 | 5.0 mg/kg | 30.16 ± 5.27* | 45.37 ± 5.48* | 57.28 ± 6.76* | 18.43 |
| Composition 9 | 5.0 mg/kg | 24.13 ± 6.48** | 36.17 ± 9.15** | 46.39 ± 8.17** | 33.94 |
| Composition 10 | 5.0 mg/kg | 30.55 ± 7.49* | 40.18 ± 7.48** | 50.38 ± 5.74* | 28.25 |
| Composition 11 | 5.0 mg/kg | 22.89 ± 7.69** | 33.67 ± 5.87** | 44.16 ± 8.76** | 37.11 |
| Composition 12 | 5.0 mg/kg | 31.25 ± 6.75** | 36.48 ± 7.01* | 50.66 ± 8.89* | 27.86 |
| Composition 13 | 5.0 mg/kg | 22.85 ± 7.68** | 35.78 ± 6.98** | 41.26 ± 6.54* | 41.24 |
| Composition 14 | 5.0 mg/kg | 30.14.19 ± 5.78 | 41.79 ± 5.87* | 52.76 ± 5.81* | 24.86 |
| Composition 15 | 5.0 mg/kg | 25.65 ± 5.27* | 40.58 ± 5.79** | 48.67 ± 8.46* | 30.69 |
| Composition 16 | 5.0 mg/kg | 20.55 ± 5.16** | 35.68 ± 4.87** | 42.36 ± 6.18** | 39.68 |
| Composition 17 | 5.0 mg/kg | 29.37 ± 6.48* | 40.69 ± 5.76** | 50.74 ± 5.71* | 27.74 |
| Composition 18 | 5.0 mg/kg | 30.75 ± 9.11* | 36.88 ± 5.97** | 49.67 ± 8.75* | 29.27 |
| Composition 19 | 5.0 mg/kg | 25.65 ± 7.48** | 32.86 ± 7.76** | 41.98 ± 7.64** | 40.22 |
| Composition 20 | 5.0 mg/kg | 31.67 ± 8.16* | 39.76 ± 8.69* | 49.97 ± 6.78* | 28.84 |
| Composition 21 | 5.0 mg/kg | 22.76 ± 5.48** | 35.49 ± 8.29** | 43.57 ± 8.14** | 37.95 |
| Composition 22 | 5.0 mg/kg | 28.69 ± 8.67* | 40.46 ± 9.17* | 54.76 ± 9.34* | 22.02 |
| Composition 23 | 5.0 mg/kg | 21.78 ± 8.13** | 35.64 ± 7.46** | 43.96 ± 7.54** | 37.40 |
| Composition 24 | 5.0 mg/kg | 28.35 ± 8.46* | 38.26 ± 9.46* | 48.56 ± 8.65* | 30.85 |
| Composition 25 | 5.0 mg/kg | 20.43 ± 5.84** | 35.15 ± 5.79** | 42.36 ± 9.44** | 39.68 |
| Composition 26 | 5.0 mgl/kg | 30.25 ± 6.74* | 40.36 ± 6.48* | 50.77 ± 6.97* | 27.70 |
| Composition 27 | 5.0 mg/kg | 31.64 ± 8.63* | 39.53 ± 8.73* | 50.65 ± 7.39* | 27.87 |
| Composition 28 | 5.0 mg/kg | 21.41 ± 6.89** | 35.67 ± 8.89** | 43.18 ± 5.68** | 38.51 |
| Composition 29 | 5.0 mg/kg | 29.17 ± 4.89* | 40.46 ± 6.47* | 52.05 ± 6.49* | 25.88 |
| Composition 30 | 5.0 mg/kg | 28.43 ± 9.33* | 41.85 ± 8.76* | 51.24 ± 8.96* | 27.03 |
| Composition 31 | 5.0 mg/kg | 22.14 ± 6.25** | 35.69 ± 4.87** | 43.45 ± 9.74** | 38.12 |
| Composition 32 | 5.0 mg/kg | 30.64 ± 8.69* | 42.56 ± 9.35* | 52.68 ± 9.57* | 24.98 |
| Composition 33 | 5.0 mg/kg | 25.16 ± 5.27** | 36.54 ± 9.64** | 45.86 ± 8.75** | 34.69 |
| Composition 34 | 5.0 mg/kg | 28.36 ± 6.48* | 40.69 ± 8.67* | 51.06 ± 8.26* | 27.29 |
| Composition 35 | 5.0 mg/kg | 20.78 ± 8.16** | 35.97 ± 8.46** | 43.96 ± 8.16** | 37.40 |
| Composition 36 | 5.0 mg/kg | 30.66 ± 8.65* | 40.38 ± 8.67* | 50.67 ± 6.67* | 27.84 |
| Composition 37 | 5.0 mg/kg | 20.40 ± 8.72** | 35.99 ± 8.37** | 42.74 ± 9.35* | 39.13 |
| Composition 38 | 5.0 mg/kg | 28.69 ± 6.58* | 36.45 ± 6.75* | 52.17 ± 9.36* | 25.70 |
| Composition 39 | 5.0 mg/kg | 26.19 ± 5.78* | 42.79 ± 6.88* | 55.38 ± 9.36* | 21.13 |
| Composition 40 | 5.0 mg/kg | 21.26 ± 5.84** | 35.39 ± 8.16** | 44.68 ± 7.04** | 36.37 |
| Composition 41 | 5.0 mg/kg | 31.25 ± 5.16 | 42.74 ± 4.87* | 56.88 ± 6.75* | 18.99 |
| Composition 42 | 5.0 mg/kg | 29.37 ± 8.67* | 40.69 ± 8.27* | 55.74 ± 9.46* | 20.62 |
| Composition 43 | 5.0 mg/kg | 21.68 ± 6.85** | 34.65 ± 8.64** | 44.77 ± 8.67** | 36.24 |
| Composition 44 | 5.0 mg/kg | 31.51 ± 5.68* | 40.86 ± 8.69* | 55.48 ± 9.74* | 20.99 |
| Composition 45 | 5.0 mg/kg | 22.15 ± 9.64** | 35.66 ± 8.67** | 44.48 ± 5.68** | 36.66 |
| Composition 46 | 5.0 mg/kg | 30.57 ± 8.56* | 41.68 ± 6.74* | 54.59 ± 6.85* | 22.26 |
| Composition 47 | 5.0 mg/kg | 21.75 ± 9.36** | 34.46 ± 9.98** | 43.76 ± 6.49** | 37.54 |
| Composition 48 | 5.0 mg/kg | 31.78 ± 9.16* | 41.75 ± 9.67* | 54.85 ± 9.37* | 21.89 |

Comparing with Saline group,
**p < 0.01,
*p < 0.05

There was a significant difference in the maximum platelet aggregation rate of the Ginkgolide B group, the Ginkgolide B+Clopidogrel group, the Ginkgolide B+Prasugrel group, the Ginkgolide B+Ticagrelor and the Ginkgolide B+Ticlopidine group, etc. when comparing with the saline group under the induction of PAF (p<0.01, p<0.05). The aggregation inhibition rate of each group was remarkably improved which means the pharmaceutic combinations of the present invention can effectively inhibit the aggregation of the platelet.

The aggregation inhibition rate of all the pharmaceutical combinations was higher than the rate of Clopidogrel group, Prasugrel group, Ticagrelor or Ticlopidine group, equivalent to that of Ginkgolide B group, some groups had even lower inhibition rate, indicating the Ginkgolide B, and Clopidogrel, Prasugrel, Ticagrelor or Ticlopidine, work synergistically;

Among the composition groups, when the weight ratio of Ginkgolide B to Clopidogrel, Prasugrel, Ticagrelor or Ticlopidine was in the range from 10:200 to 20:50, the platelet aggregation inhibition rate was relative high (For Clopidogrel, please refer to groups 1, 4, 7, 9, 11). When the weight ratio of Ginkgolide B to Clopidogrel, Prasugrel, Ticagrelor or Ticlopidine was 10:200, the platelet aggregation inhibition rate was the highest (For Clopidogrel, please refer to group 1). Therefore, the preferable weight ratio of Ginkgolide B to Clopidogrel, Prasugrel, Ticagrelor or Ticlopidine was in the range from 10:200 to 20:50, more preferably 10:200. When the weight ratio of Ginkgolide B to Clopidogrel, Prasugrel, Ticagrelor or Ticlopidine was in the range from 10:200 to 20:50, the usage of Ginkgolide B was less than the usage of Clopidogrel, Prasugrel, Ticagrelor or Ticlopidine, but the aggregation inhibition rate was much higher than the that of groups with the same amount of Clopidogrel, Prasugrel, Ticagrelor or Ticlopidine, and was equivalent to the group of with the same usage of Ginkgolide B. This means the synergetic effect between Ginkgolide B and Clopidogrel, Prasugrel, Ticagrelor or Ticlopidine was very strong when used in this range of weight ratio.

In addition, the aggregation inhibition rate of the group of Ginkgolide B+Ticlopidine (Composition 37) was higher than that of Extraction combination group (Jinnaduo+Asprin), indicating the synergistic effect of Ginkgolide B and Aspirin was better than that of Jinnaduo and Aspirin.

2. 2 Result of Electron Microscope Study of Platelets
The result is shown in Table.2:

TABLE 2

Morphology of platelet of each group after the addition of PAF

| Group | Types of morphology (%) | | | |
|---|---|---|---|---|
| | Circle | Tree like | Flat | Aggregated |
| Saline | 3.2 ± 0.8 | 7.5 ± 2.4 | 11.8 ± 3.2 | 77.5 ± 18.5 |
| Ginkgolide B | 31.6 ± 6.1** | 15.8 ± 6.8* | 46.1 ± 8.3** | 22.3 ± 9.6** |
| Clopidogrel | 7.7 ± 7.8 | 24.6 ± 8.8** | 30.7 ± 13.6** | 37.0 ± 14.9** |
| Prasugrel | 9.9 ± 7.6* | 19.6 ± 6.8** | 25.4 ± 8.7* | 45.1 ± 9.4* |
| Ticagrelor | 6.2 ± 7.5 | 21.4 ± 9.4** | 33.6 ± 10.7** | 38.8 ± 11.1** |
| Ticlopidine | 6.5 ± 9.4 | 23.1 ± 6.8** | 25.9 ± 8.7* | 44.5 ± 8.9* |
| Jinnaduo | 11.2 ± 9.6** | 23.4 ± 9.0** | 35.8 ± 11.0** | 29.6 ± 10.4** |
| Extraction combination | 15.6 ± 7.3** | 27.4 ± 9.4** | 28.7 ± 9.5** | 28.3 ± 6.8** |
| Composition 1 | 35.9 ± 11.7** | 20.4 ± 9.5** | 15.3 ± 8.6 | 28.4 ± 10.7** |
| Composition 2 | 12.3 ± 9.2** | 22.6 ± 7.8** | 33.3 ± 7.9** | 31.8 ± 10.2** |
| Composition 3 | 10.7 ± 6.6* | 29.3 ± 6.8** | 26.4 ± 8.4** | 33.6 ± 8.4** |
| Composition 4 | 9.6 ± 5.7* | 26.5 ± 6.7** | 34.3 ± 8.6** | 29.6 ± 6.4** |
| Composition 5 | 7.1 ± 7.6 | 26.4 ± 9.3** | 30.4 ± 8.6** | 36.1 ± 8.7** |
| Composition 6 | 8.3 ± 5.9* | 25.5 ± 5.8** | 29.7 ± 8.1* | 36.5 ± 7.7** |
| Composition 7 | 9.3 ± 6.9** | 25.7 ± 7.3** | 35.6 ± 7.8** | 29.4 ± 6.8** |
| Composition 8 | 17.8 ± 8.7** | 17.6 ± 8.4** | 28.4 ± 7.5* | 36.2 ± 9.1** |
| Composition 9 | 15.3 ± 9.6** | 19.4 ± 5.7** | 30.8 ± 9.5* | 34.5 ± 9.2** |
| Composition 10 | 7.4 ± 9.7 | 25.3 ± 6.8** | 30.4 ± 7.6* | 36.9 ± 9.6** |
| Composition 11 | 8.7 ± 6.8* | 27.0 ± 9.7** | 31.2 ± 6.8** | 33.1 ± 9.1** |
| Composition 12 | 10.3 ± 8.3** | 27.5 ± 9.4** | 32.7 ± 5.4** | 29.5 ± 9.6** |
| Composition 13 | 12.2 ± 5.4** | 34.5 ± 8.9** | 31.5 ± 8.6** | 21.8 ± 6.8** |
| Composition 14 | 15.1 ± 5.8** | 23.6 ± 7.2** | 30.7 ± 8.1** | 30.6 ± 8.3** |
| Composition 15 | 13.0 ± 7.5** | 24.6 ± 7.8** | 29.3 ± 6.8** | 33.1 ± 8.5** |
| Composition 16 | 13.4 ± 8.6** | 25.6 ± 6.4* | 35.4 ± 7.9** | 25.6 ± 9.6** |
| Composition 17 | 6.1 ± 3.8 | 20.7 ± 8.4** | 36.4 ± 7.8** | 36.8 ± 9.8** |
| Composition 18 | 10.1 ± 6.9** | 28.6 ± 12.1** | 25.9 ± 5.7** | 35.4 ± 9.5** |
| Composition 19 | 6.5 ± 7.1 | 30.7 ± 6.3** | 36.4 ± 6.9** | 26.4 ± 5.8** |
| Composition 20 | 15.5 ± 5.6** | 23.5 ± 8.6** | 20.4 ± 8.2** | 40.6 ± 5.3** |
| Composition 21 | 10.3 ± 6.3** | 22.3 ± 5.2** | 32.8 ± 8.7** | 34.6 ± 9.4** |
| Composition 22 | 12.4 ± 7.8** | 25.6 ± 8.9** | 22.2 ± 8.9** | 39.8 ± 13.0** |
| Composition 23 | 13.4 ± 7.6** | 29.6 ± 9.6** | 30.6 ± 9.6** | 26.4 ± 10.4** |
| Composition 24 | 6.5 ± 8.8 | 26.4 ± 7.9** | 30.4 ± 5.5** | 36.7 ± 9.8** |
| Composition 25 | 16.2 ± 8.4** | 26.5 ± 7.8** | 31.7 ± 9.7** | 25.6 ± 8.7** |
| Composition 26 | 7.9 ± 8.6 | 24.6 ± 8.6** | 32.4 ± 9.5* | 35.1 ± 5.9** |
| Composition 27 | 7.4 ± 9.7 | 25.3 ± 6.8** | 30.4 ± 7.6* | 36.9 ± 9.6** |
| Composition 28 | 9.2 ± 8.9* | 27.4 ± 8.6** | 35.6 ± 8.4** | 27.8 ± 9.1** |
| Composition 29 | 10.3 ± 8.3* | 26.8 ± 9.4** | 28.1 ± 8.7** | 34.8 ± 9.6** |
| Composition 30 | 10.7 ± 9.8** | 22.6 ± 9.6** | 30.2 ± 7.6** | 36.5 ± 8.7** |
| Composition 31 | 9.7 ± 6.9** | 31.3 ± 7.2** | 30.4 ± 8.1** | 28.6 ± 7.6** |
| Composition 32 | 11.3 ± 7.3** | 20.9 ± 8.9** | 34.7 ± 8.7** | 33.1 ± 5.6** |
| Composition 33 | 13.4 ± 8.6** | 25.6 ± 6.4* | 35.4 ± 7.9** | 25.6 ± 9.6** |
| Composition 34 | 11.7 ± 9.4* | 21.6 ± 7.6** | 34.6 ± 9.1** | 32.1 ± 8.7** |
| Composition 35 | 19.3 ± 8.8** | 26.8 ± 9.0** | 26.4 ± 8.1** | 27.5 ± 8.7** |
| Composition 36 | 14.3 ± 8.1* | 20.4 ± 8.9** | 30.5 ± 8.7** | 34.8 ± 7.6** |
| Composition 37 | 13.5 ± 8.5** | 30.1 ± 4.9** | 31.8 ± 7.7** | 24.6 ± 6.4** |
| Composition 38 | 11.0 ± 8.6** | 16.9 ± 7.6** | 36.4 ± 9.2** | 35.7 ± 8.2** |
| Composition 39 | 8.5 ± 4.7* | 25.2 ± 10.0** | 29.5 ± 7.1** | 36.8 ± 11.4** |
| Composition 40 | 13.2 ± 8.0** | 30.6 ± 7.8** | 29.8 ± 11.4** | 26.4 ± 8.3** |
| Composition 41 | 7.6 ± 9.3 | 29.0 ± 6.4** | 29.5 ± 7.1** | 33.9 ± 7.6** |
| Composition 42 | 8.0 ± 7.9** | 30.8 ± 8.6** | 24.8 ± 9.3** | 36.4 ± 9.5** |
| Composition 43 | 14.8 ± 7.1* | 23.4 ± 7.9** | 36.0 ± 9.9** | 25.8 ± 8.3** |
| Composition 44 | 6.9 ± 7.6 | 26.9 ± 8.6** | 30.6 ± 8.4** | 35.8 ± 8.0** |
| Composition 45 | 11.1 ± 7.2** | 25.6 ± 7.1** | 35.6 ± 9.5** | 27.7 ± 8.1** |
| Composition 46 | 7.3 ± 5.9 | 26.7 ± 10.0** | 30.4 ± 8.4** | 35.6 ± 10.1** |
| Composition 47 | 11.6 ± 5.2** | 31.1 ± 8.6** | 30.9 ± 5.7** | 26.4 ± 9.8** |
| Composition 48 | 12.7 ± 8.6** | 26.8 ± 8.5** | 25.9 ± 7.6** | 34.6 ± 5.8** |

Comparing with Saline group,
**p < 0.01,
*p < 0.05

Four types of platelet morphology were observed under 2000-fold scanning electron microscope: Circle type, Tree like type, Flat type and Aggregated type. Under induction of PAF, the platelets in the saline group were strongly activated, with enhanced adhesion, and red blood cells can be seen to adhere to the platelets; the platelets were irregular in shape with enlarged size, and the formation of spore-like pseudopodium and increased number of Aggregated type of platelets were observed. The platelets were in a similar size and had a smooth surface in the Ginkgolide B group, the Clopidogrel group, the Prasugrel group, the Ticagrelor group, the Ticlopidine group, the Ginkgolide B+Clopidogrel groups, the Ginkgolide B+Prasugrel groups, the Ginkgolide B+Ticagrelor groups, the Ginkgolide B+Ticlopidine groups, and the Aggregated type platelets were rarely seen, indicating the compositions of the present invention can effectively inhibit the aggregation of platelet.

The Aggregated type platelets in each of the composition groups were less than in the Clopidogrel group, Prasugrel group, Ticagrelor or Ticlopidine group, and equivalent to that of Ginkgolide B group, some groups had even less Aggregated type platelets, indicating the Ginkgolide B and Clopidogrel, Prasugrel, Ticagrelor or Ticlopidine work synergistically;

Among the composition groups, when the weight ratio of Ginkgolide B to Clopidogrel, Prasugrel, Ticagrelor or Ticlopidine was in the range from 10:200 to 20:50, the number of Aggregated type platelets was low (For Clopidogrel, please refer to group 1, 4, 7, 9, 11). When the weight ratio of Ginkgolide B to Clopidogrel, Prasugrel, Ticagrelor or Ticlopidine was 10:200, the number of Aggregated type platelets was the lowest (For Clopidogrel, please refer to group 1). Therefore, the preferable weight ratio of Ginkgolide B to Clopidogrel, Prasugrel, Ticagrelor or Ticlopidine was in the range from 10:200 to 20:50, more preferably 10:200. When the weight ratio of Ginkgolide B to Clopidogrel, Prasugrel, Ticagrelor or Ticlopidine was in the range from 10:200 to 20:50, the usage of Ginkgolide B was less than the usage of Clopidogrel, Prasugrel, Ticagrelor or Ticlopidine, but the number of Aggregated type platelets was a lot less than the that of groups with the same amount of Clopidogrel, Prasugrel, Ticagrelor or Ticlopidine, and was equivalent to the group of with the same usage of Ginkgolide B. This means the synergetic effect between Ginkgolide B, and Clopidogrel, Prasugrel, Ticagrelor or Ticlopidine was very strong when used in this range of weight ratio.

In addition, the aggregation inhibition rate of the group of Ginkgolide B+Ticlopidine (Composition 37) was higher than that of Extraction combination group (Jinnaduo+Asprin), indicating the synergistic effect of Ginkgolide B and Aspirin was better than that of Jinnaduo and Aspirin.

2.3 Result of the Level of PF-4 and β-TG

The result is shown in Table.3:

TABLE 3

The level of PF-4 and β-TG

| Group | PF-4 (μg/ml) | B-TG (μg/ml) |
|---|---|---|
| Saline | 1.733 ± 0.294 | 1.740 ± 0.215 |
| Ginkgolide B | 1.264 ± 0.215** | 1.247 ± 0.184** |
| Clopidogrel | 1.506 ± 0.216 | 1.588 ± 0.209 |
| Prasugrel | 1.497 ± 0.315 | 1.514 ± 0.173 |
| Ticagrelor | 1.466 ± 0.203 | 1.565 ± 0.268 |
| Ticlopidine | 1.502 ± 0.324 | 1.550 ± 0.136 |
| Jinnaduo | 1.525 ± 0.170 | 1.472 ± 0.153* |
| Extraction combination | 1.398 ± 0.154* | 1.431 ± 0.177* |
| Composition 1 | 1.128 ± 0.135** | 1.197 ± 0.151** |
| Composition 2 | 1.343 ± 0.176* | 1.396 ± 0.207* |
| Composition 3 | 1.325 ± 0.118* | 1.359 ± 0.149* |
| Composition 4 | 1.199 ± 0.167** | 1.246 ± 0.174** |
| Composition 5 | 1.283 ± 0.159** | 1.306 ± 0.193** |
| Composition 6 | 1.291 ± 0.145** | 1.315 ± 0.177** |
| Composition 7 | 1.187 ± 0.162** | 1.206 ± 0.176** |
| Composition 8 | 1.336 ± 0.144* | 1.359 ± 0.148* |
| Composition 9 | 1.201 ± 0.184** | 1.275 ± 0.138** |
| Composition 10 | 1.374 ± 0.218* | 1.398 ± 0.205* |
| Composition 11 | 1.233 ± 0.174** | 1.259 ± 0.186** |
| Composition 12 | 1.299 ± 0.146** | 1.310 ± 0.143* |
| Compositiou 13 | 1.155 ± 0.168** | 1.181 ± 0.137** |
| Compositiott 14 | 1.310 ± 0.175* | 1.359 ± 0 164* |
| Composition 15 | 1.287 ± 0.153** | 1.294 ± 0.148** |
| Compositiou 16 | 1.154 ± 0.135** | 1.236 ± 0.139** |
| Composition 17 | 1.296 ± 0.164** | 1.335 ± 0.146* |
| Composition 18 | 1.325 ± 0.142* | 1.358 ± 0.217* |
| Composition 19 | 1.221 ± 0.264** | 1.245 ± 0.237** |
| Composition 20 | 1.374 ± 0.265* | 1.392 ± 0.248* |
| Composition 21 | 1.259 ± 0.163** | 1.294 ± 0.324** |
| Composition 22 | 1.328 ± 0.215* | 1.359 ± 0.240* |
| Composition 23 | 1.198 ± 0.317** | 1.213 ± 0.125** |
| Composition 24 | 1.286 ± 0.241** | 1.297 ± 0.312** |
| Composition 25 | 1.156 ± 0.138** | 1.176 ± 0.135** |
| Composition 26 | 1.338 ± 0.164* | 1.376 ± 0.126** |
| Composition 27 | 1.369 ± 0.185* | 1.384 ± 0.242* |
| Composition 28 | 1.202 ± 0.106* | 1.257 ± 0.264* |
| Composition 29 | 1.375 ± 0.275* | 1.395 ± 0.169* |

TABLE 3-continued

The level of PF-4 and β-TG

| Group | PF-4 (μg/ml) | B-TG (μg/ml) |
|---|---|---|
| Composition 30 | 1.346 ± 0.165* | 1.376 ± 0.188* |
| Composition 31 | 1.191 ± 0.245** | 1.215 ± 0.157* |
| Composition 32 | 1.290 ± 0.154** | 1.304 ± 0.235* |
| Composition 33 | 1.175 ± 0.235** | 1.185 ± 0.136** |
| Composition 34 | 1.287 ± 0.236** | 1.294 ± 0.247** |
| Composition 35 | 1.183 ± 0.226** | 1.206 ± 0.316** |
| Composition 36 | 1.308 ± 0.154* | 1.359 ± 0.173* |
| Composition 37 | 1.146 ± 0.152** | 1.203 ± 0.157* |
| Composition 38 | 1.305 ± 0.167* | 1.352 ± 0.145* |
| Composition 39 | 1.321 ± 0.134* | 1.347 ± 0.138* |
| Composition 40 | 1.185 ± 0.126** | 1.192 ± 0.135** |
| Composition 41 | 1.246 ± 0.241** | 1.281 ± 0.150** |
| Composition 42 | 1.301 ± 0.161* | 1.342 ± 0.186* |
| Composition 43 | 1.172 ± 0.133** | 1.203 ± 0.164** |
| Composition 44 | 1.301 ± 0.225* | 1.324 ± 0.215* |
| Composition 45 | 1.201 ± 0.274** | 1.256 ± 0.276** |
| Composition 46 | 1.299 ± 0.175** | 1.307 ± 0.243* |
| Composition 47 | 1.175 ± 0.134** | 1.195 ± 0.236** |
| Composition 48 | 1.314 ± 0.303* | 1.356 ± 0.112* |

Comparing with Saline group, **p+210.01, *p+210.05

The decreased level of PF-4 and β-TG indicating the release ability of platelet is inhibited.

Compared with the saline group, the levels of PF-4 and β-TG of the Ginkgolide B group, the Ginkgolide B+Clopidogrel groups, the Ginkgolide B+Prasugrel groups, the Ginkgolide B+Ticagrelor groups, the Ginkgolide B+Ticlopidine groups decreased significantly (p<0.01, p<0.05); while the level of the Clopidogrel group, the Prasugrel group, the Ticagrelor group or the Ticlopidine group didn't decrease significantly, indicating the compositions of the present invention can effectively inhibit the aggregation of platelet.

The levels of PF-4 and β-TG of each of the composition groups were less than those in the Clopidogrel group, Prasugrel group, Ticagrelor group or Ticlopidine group, and were equivalent to those of Ginkgolide group, the levels of PF-4 and β-TG of some groups were even lower, indicating the Ginkgolide B, and Clopidogrel, Prasugrel, Ticagrelor or Ticlopidine work synergistically;

Among the composition groups, when the weight ratio of Ginkgolide B to Clopidogrel, Prasugrel, Ticagrelor or Ticlopidine was in the range from 10:200 to 20:50, the levels of PF-4 and β-TG were low (For Clopidogrel, please refer to group 1, 4, 7, 9, 11). When the weight ratio of Ginkgolide B to Clopidogrel, Prasugrel, Ticagrelor or Ticlopidine was 10:200, the levels of PF-4 and β-TG were at lowest (For Clopidogrel, please refer to group 1). Therefore, the preferable weight ratio of Ginkgolide B to Clopidogrel, Prasugrel, Ticagrelor or Ticlopidine was in the range from 10:200 to 20:50, more preferably 10:200. When the weight ratio of Ginkgolide B to Clopidogrel, Prasugrel, Ticagrelor or Ticlopidine was in the range from 10:200 to 20:50, the usage of Ginkgolide B was less than the usage of Clopidogrel, Prasugrel, Ticagrelor or Ticlopidine, but the levels of PF-4 and β-TG were a lot less than those of groups with the same amount of Clopidogrel, Prasugrel, Ticagrelor or Ticlopidine, and was equivalent to the group of with the same usage of Ginkgolide B. This means the synergetic effect between Ginkgolide B and Clopidogrel, Prasugrel, Ticagrelor or Ticlopidine was very strong when used in this range of weight ratio.

In addition, the levels of PF-4 and β-TG of the group of Ginkgolide B+Ticlopidine (Composition 37) was lower than those of Extraction combination group (Jinnaduo+Asprin), indicating the synergistic effect of Ginkgolide B and Aspirin was better than that of Jinnaduo and Aspirin.

In conclusion, Ginkgolide B and adenosine diphosphate receptor antagonist are used in combination in the present invention, and a synergistic effect is achieved. The pharmaceutical composition comprising Ginkgolide B and adenosine diphosphate receptor antagonist of the present invention effectively inhibits the platelet aggregation, which has an excellent effect and a prominent prospect of clinical application.

The invention claimed is:

1. A pharmaceutical composition containing Ginkgolide B, wherein the pharmaceutical composition comprises Ginkgolide B and Clopidogrel.

2. The pharmaceutical composition of claim 1, wherein Ginkgolide B is present in an amount of 1-20 parts by weight, and Clopidogrel, is present in an amount of 50-500 parts by weight.

3. The pharmaceutical composition of claim 2, wherein Ginkgolide B is present in an amount of 5-15 parts by weight and Clopidogrel is present in an amount of 100-400 by weight.

4. The pharmaceutical composition of claim 3, wherein Ginkgolide B is present in an amount of 8-12 parts by weight and Clopidogrel is present in an amount of 150-300 parts by weight.

5. The pharmaceutical composition of claim 4, wherein Ginkgolide B is present in an amount of 10 parts by weight and Clopidogrel is present in an amount of 200 by weight.

6. The pharmaceutical composition of claim 2, wherein a weight ratio of Ginkgolide B to Clopidogrel is in the range from 10:200 to 20:50.

7. A method for preparing the pharmaceutical composition of claim 1, comprising the following steps:
    S1: weighing out raw materials of Ginkgolide B and Clopidogrel according to the predetermined parts by weight; and
    S2: mixing the raw materials, and adding a pharmaceutically acceptable auxiliary to the raw materials to prepare a common pharmaceutical preparation.

8. A method for preparing the pharmaceutical composition of claim 2, comprising the following steps:
    S1: weighing out raw materials of Ginkgolide B and Clopidogrel according to the predetermined parts by weight; and
    S2: mixing the raw materials, and adding a pharmaceutically acceptable auxiliary to the raw materials to prepare a common pharmaceutical preparation.

9. A method for preparing the pharmaceutical composition of claim 6, comprising the following steps:
    S1: weighing out raw materials of Ginkgolide B and Clopidogrel according to the predetermined parts by weight; and
    S2: mixing the raw materials, and adding a pharmaceutically acceptable auxiliary to the raw materials to prepare a common pharmaceutical preparation.

10. A method for anti-platelet aggregation, comprising administering the pharmaceutical composition of claim 1 to a subject.

11. A method for anti-platelet aggregation, comprising administering the pharmaceutical composition of claim 2 to a subject.

12. A method for anti-platelet aggregation, comprising administering the pharmaceutical composition of claim 6 to a subject.

* * * * *